US008822727B2

(12) United States Patent
Carlos et al.

(10) Patent No.: US 8,822,727 B2
(45) Date of Patent: Sep. 2, 2014

(54) PROCESSES FOR THE PREPARATION OF INTERMEDIATES RELATED TO THE 5-HT$_{2C}$ AGONIST (R)-8-CHLORO-1-METHYL-2,3,4,5-TETRAHYDRO-1H-3-BENZAZEPINE

(75) Inventors: Marlon V. Carlos, Chula Vista, CA (US); Ryan O. Castro, San Diego, CA (US); Tawfik Gharbaoui, Escondido, CA (US); Xiao-Xiong Lu, San Diego, CA (US); You-An Ma, Poway, CA (US); Nicholas D. San Martin, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 352 days.

(21) Appl. No.: 12/921,101

(22) PCT Filed: Mar. 3, 2009

(86) PCT No.: PCT/US2009/001340
§ 371 (c)(1),
(2), (4) Date: Oct. 4, 2010

(87) PCT Pub. No.: WO2009/111004
PCT Pub. Date: Sep.a 11, 2009

(65) Prior Publication Data
US 2011/0015438 A1    Jan. 20, 2011

Related U.S. Application Data

(60) Provisional application No. 61/068,102, filed on Mar. 4, 2008.

(51) Int. Cl.
*C07C 211/00* (2006.01)
(52) U.S. Cl.
USPC .......................................................... 564/366
(58) Field of Classification Search
CPC ................................ C07C 17/18; C07C 51/60
See application file for complete search history.

(56) References Cited

U.S. PATENT DOCUMENTS

| | | |
|---|---|---|
| 2,900,415 A | 8/1959 | Biel |
| 3,652,543 A | 3/1972 | Hoegerle |
| 3,716,639 A | 2/1973 | Hoegerle et al. |
| 3,795,683 A | 3/1974 | Brossi et al. |
| 4,108,989 A | 8/1978 | Holden |
| 4,111,957 A | 9/1978 | Holden et al. |
| 4,210,729 A | 7/1980 | Hermans et al. |
| 4,210,749 A | 7/1980 | Shetty |
| 4,233,217 A | 11/1980 | Shetty |
| 4,477,378 A | 10/1984 | Gold et al. |
| 4,541,954 A | 9/1985 | Borowski et al. |
| 4,584,293 A | 4/1986 | Reiffen et al. |
| 4,737,495 A | 4/1988 | Bomhard et al. |
| 4,762,845 A | 8/1988 | Chu et al. |
| 4,957,914 A | 9/1990 | Clark et al. |
| 4,988,690 A | 1/1991 | Effland et al. |
| 5,015,639 A | 5/1991 | Berger et al. |
| 5,178,786 A | 1/1993 | Jahnke et al. |
| 5,247,080 A | 9/1993 | Berger et al. |
| 5,275,915 A | 1/1994 | Kojima et al. |
| 5,387,685 A | 2/1995 | Powell et al. |
| 5,397,793 A | 3/1995 | Shaber et al. |
| 5,412,119 A | 5/1995 | Brussee et al. |
| 5,422,355 A | 6/1995 | White et al. |
| 5,691,362 A | 11/1997 | McCormick et al. |
| 5,750,520 A | 5/1998 | Danilewicz et al. |
| 5,795,895 A | 8/1998 | Anchors |
| 5,856,503 A | 1/1999 | Aebi et al. |
| 5,861,393 A | 1/1999 | Danilewicz et al. |
| 5,908,830 A | 6/1999 | Smith et al. |
| 5,925,651 A | 7/1999 | Hutchinson |
| 5,939,415 A | 8/1999 | Laufer et al. |
| 5,942,535 A | 8/1999 | Laufer et al. |
| 5,958,943 A | 9/1999 | Laufer et al. |
| 6,087,346 A | 7/2000 | Glennon et al. |
| 6,218,385 B1 | 4/2001 | Adam et al. |
| 6,900,313 B2 | 5/2005 | Wasserscheid et al. |
| 6,953,787 B2 | 10/2005 | Smith et al. |
| 6,972,295 B2 | 12/2005 | Hagmann et al. |
| 7,105,523 B2 | 9/2006 | Stasch et al. |
| 7,157,466 B2 | 1/2007 | McClure et al. |
| 7,173,037 B2 | 2/2007 | Alonso-Alija et al. |
| 7,211,591 B2 | 5/2007 | Tajima et al. |
| 7,229,991 B2 | 6/2007 | Merla et al. |
| 7,230,024 B2 | 6/2007 | Carpino et al. |
| 7,232,823 B2 | 6/2007 | Carpino et al. |

(Continued)

FOREIGN PATENT DOCUMENTS

| | | |
|---|---|---|
| AU | 515 236 B2 | 3/1981 |
| CA | 1090797 | 12/1980 |

(Continued)

OTHER PUBLICATIONS

March, J. Advanced Organic Chemistry 4$^{th}$ Edition, 1992, front matter and pp. 431-433.*
U.S. Appl. No. 60/372,058, filed Apr. 12, 2002, Smith et al.
U.S. Appl. No. 60/405,495, filed Aug. 23, 2002, Smith et al.
U.S. Appl. No. 60/434,607, filed Dec. 18, 2002, Smith et al.
U.S. Appl. No. 60/476,280, filed Jun. 17, 2003, Smith et al.
U.S. Appl. No. 60/512,967, filed Oct. 21, 2003, Burbaum et al.
U.S. Appl. No. 60/638,221, filed Dec. 21, 2004, Agarwal et al.
U.S. Appl. No. 60/789,191, filed Apr. 3, 2006, Lu et al.
U.S. Appl. No. 60/873,036, filed Dec. 5, 2006, Gharbaoui et al.
U.S. Appl. No. 61/068,102, filed Mar. 4, 2008, Carlos et al.
U.S. Appl. No. 61/268,930, filed Jun. 18, 2009, Demattei et al.
"Arena Pharmaceuticals Announces Results of its Phase 1b Safety Study for its Novel Anti-Obesity Compound," Press Release, Nov. 30, 2004, 2 pages.
"Arena Pharmaceuticals Initiates Clinical Trial of Novel Anti-Obesity Drug," Press Release, Feb. 24, 2004, 1 page.
"Arena Pharmaceuticals Initiates Phase 1b Clinical Trial of Novel Anti-Obesity Drug," Press Release, Jul. 26, 2004, 1 page.
"Arena Pharmaceuticals Initiates Phase 2 Efficacy Study for its Novel Anti-Obesity Compound," Press Release, Dec. 22, 2004, 2 pages.

(Continued)

*Primary Examiner* — Clinton Brooks

(57) ABSTRACT

The present invention provides processes and intermediates useful in the preparation of 8-chloro-1-methyl-2,3,4,5-tetrahydro-1H-3-benzazepine, a serotonin (5-HT) receptor agonist that is useful in the treatment or prophylaxis of, for example, central nervous system disorders, such as obesity.

29 Claims, No Drawings

(56) References Cited

U.S. PATENT DOCUMENTS

| | | |
|---|---|---|
| 7,514,422 B2 | 4/2009 | Smith et al. |
| 7,704,993 B2 | 4/2010 | Smith et al. |
| 7,977,329 B2 | 7/2011 | Smith et al. |
| 8,153,621 B2 | 4/2012 | Behan et al. |
| 8,168,624 B2 | 5/2012 | Agarwal et al. |
| 8,168,782 B2 | 5/2012 | Weigl et al. |
| 8,207,158 B2 | 6/2012 | Smith et al. |
| 8,273,734 B1 | 9/2012 | Smith et al. |
| 8,299,241 B2 | 10/2012 | Gharbaoui et al. |
| 2003/0105106 A1 | 6/2003 | Chiang et al. |
| 2003/0225057 A1 | 12/2003 | Smith et al. |
| 2004/0101575 A1 | 5/2004 | Hinz |
| 2005/0020573 A1 | 1/2005 | Smith et al. |
| 2007/0060568 A1 | 3/2007 | Smith et al. |
| 2007/0275949 A1 | 11/2007 | Smith et al. |
| 2008/0009478 A1 | 1/2008 | Smith et al. |
| 2008/0045502 A1 | 2/2008 | Wolgast et al. |
| 2009/0143576 A1 | 6/2009 | Weigl et al. |
| 2010/0004223 A1 | 1/2010 | Agarwal et al. |
| 2010/0173894 A1 | 7/2010 | Smith et al. |
| 2010/0305316 A1 | 12/2010 | Gharbaoui et al. |
| 2011/0015438 A1 | 1/2011 | Carlos et al. |
| 2012/0135982 A1 | 5/2012 | Smith et al. |
| 2012/0142967 A1 | 6/2012 | De Mattei et al. |
| 2012/0252786 A1 | 10/2012 | Behan et al. |
| 2012/0252787 A1 | 10/2012 | Anderson et al. |
| 2012/0252788 A1 | 10/2012 | Smith et al. |
| 2012/0264743 A1 | 10/2012 | Agarwal et al. |

FOREIGN PATENT DOCUMENTS

| | | |
|---|---|---|
| CA | 2197789 | 2/1996 |
| CA | 2325741 | 10/1999 |
| CH | 500194 | 1/1971 |
| CN | 102126988 | 7/2011 |
| DE | 1944121 | 3/1970 |
| DE | 1914456 | 6/1971 |
| DE | 3315106 A1 | 11/1983 |
| DE | 3418270 A1 | 11/1985 |
| EP | 0 002 765 A1 | 7/1979 |
| EP | 0 027 695 B1 | 10/1980 |
| EP | 0 007 070 A1 | 1/1983 |
| EP | 0 161 350 A1 | 11/1985 |
| EP | 0 174 118 A3 | 3/1986 |
| EP | 0 080 779 B1 | 7/1986 |
| EP | 0 204 349 A2 | 12/1986 |
| EP | 0 096 838 A1 | 4/1987 |
| EP | 0 245 997 A2 | 11/1987 |
| EP | 0 285 287 A2 | 10/1988 |
| EP | 0 285 287 A3 | 10/1988 |
| EP | 0 331 130 A1 | 9/1989 |
| EP | 0 331 130 B1 | 9/1993 |
| EP | 0 285 919 B1 | 10/1994 |
| EP | 0 987 235 A1 | 3/2000 |
| EP | 1 074 549 A2 | 2/2001 |
| EP | 0 987 235 B1 | 3/2003 |
| EP | 1 074 549 B1 | 11/2003 |
| EP | 1 411 881 A2 | 4/2004 |
| EP | 1 411 881 B1 | 5/2005 |
| EP | 1 838 677 B1 | 9/2009 |
| FR | 2 518 544 A1 | 6/1983 |
| GB | 1196229 | 6/1970 |
| GB | 1221324 | 2/1971 |
| GB | 1225053 | 3/1971 |
| GB | 1247306 | 9/1971 |
| GB | 1268243 | 3/1972 |
| GB | 1542317 | 3/1979 |
| GB | 1599705 | 10/1981 |
| GB | 2133401 | 7/1984 |
| JP | 62-267250 | 11/1987 |
| JP | 2-502723 | 8/1990 |
| JP | 5-339263 | 12/1993 |
| JP | 6-62574 | 8/1994 |
| JP | 6-298746 | 10/1994 |
| JP | 8-134048 | 5/1996 |
| JP | 9-30960 | 2/1997 |
| JP | 9-87258 | 3/1997 |
| JP | 2000-44533 | 2/2000 |
| JP | 2001-76413 | 3/2001 |
| JP | 2001-89472 | 4/2001 |
| JP | 2003-34681 | 2/2003 |
| JP | 2000-159702 | 6/2003 |
| JP | 2004-155744 | 6/2004 |
| JP | 2007-223983 | 9/2007 |
| NL | 7807819 | 7/1978 |
| SU | 1238732 A3 | 6/1986 |
| WO | WO 88/07526 A1 | 10/1988 |
| WO | WO 88/07858 A1 | 10/1988 |
| WO | WO 91/19698 A1 | 12/1991 |
| WO | WO 93/00094 A2 | 1/1993 |
| WO | WO 93/03015 A1 | 2/1993 |
| WO | WO 93/16997 A1 | 9/1993 |
| WO | WO 95/13274 A1 | 5/1995 |
| WO | WO 96/04271 A1 | 2/1996 |
| WO | WO 96/05194 A1 | 2/1996 |
| WO | WO 96/33993 A1 | 10/1996 |
| WO | WO 97/24364 A1 | 7/1997 |
| WO | WO 98/06701 A1 | 2/1998 |
| WO | WO 98/40385 A1 | 9/1998 |
| WO | WO 99/24411 A1 | 5/1999 |
| WO | WO 02/40471 A2 | 5/2002 |
| WO | WO 02/48124 A2 | 6/2002 |
| WO | WO 02/074746 A1 | 9/2002 |
| WO | WO 03/000663 A1 | 1/2003 |
| WO | WO 03/027068 A2 | 4/2003 |
| WO | WO 03/057161 A2 | 7/2003 |
| WO | WO 03/062205 A1 | 7/2003 |
| WO | WO 03/062392 A2 | 7/2003 |
| WO | WO 03/086306 A2 | 10/2003 |
| WO | WO 03/086306 A3 | 2/2004 |
| WO | WO 2004/037788 A1 | 5/2004 |
| WO | WO 2005/003096 A1 | 1/2005 |
| WO | WO 2005/019179 A2 | 3/2005 |
| WO | WO 2005/019179 A3 | 3/2005 |
| WO | WO 2005/019180 A1 | 3/2005 |
| WO | WO 2005/042490 A1 | 5/2005 |
| WO | WO 2005/042491 A1 | 5/2005 |
| WO | WO 2005/082859 A1 | 9/2005 |
| WO | WO 2006/006933 A2 | 1/2006 |
| WO | WO 2006/013209 A2 | 2/2006 |
| WO | WO 2006/043710 A1 | 4/2006 |
| WO | WO 2006/069363 A2 | 6/2006 |
| WO | WO 2006/071740 A2 | 7/2006 |
| WO | WO 2006/069363 A3 | 5/2007 |
| WO | WO 2007/120517 A2 | 10/2007 |
| WO | WO 2007/120517 A3 | 6/2008 |
| WO | WO 2008/070111 A2 | 6/2008 |
| WO | WO 2008/070111 A3 | 8/2008 |
| WO | WO 2009/111004 A1 | 9/2009 |
| WO | WO 2010/148207 A2 | 12/2010 |

OTHER PUBLICATIONS

"Arena Pharmaceuticals Reports Successful Phase 1a Safety and Clinical Pharmacology Trial Results of Novel Anti-Obesity Compound," Press Release, Jul. 14, 2004, 2 pages.

"Silver Lining to the Cloud Over Anorexogen-Related Cardiac Valvulpathy?" Editorial, Annals of Internal Medicine, 134(4): 335-337 (2001).

Bagnol et al., "Obesity and Hypothalamic Signaling: Role of GPCRs," Presentation, Arena Pharmaceuticals, Inc., Jul. 30, 2010, 30 pages.

Baindur et al., "(±)-3-Allyl-7-halo-8-hydroxy-1-phenyl-2,3,4,5-tetrahydro-1H-3-benzazepines as Selective High Affinity D1 Dopamine Receptor Antagonists: Synthesis and Structure-Activity Relationship," J. Med. Chem., 35:67-72 (1992).

Barbière, "Estérification Nitrique et Nitration d'Amino-alcools," Bulletin de la Société Chimique de France, 5(11):470-480 (1944).

Barnes, "Pharmacological Strategies for Relapse Prevention in Schizophrenia," Psychiatry 3(10): 37-40 (2004).

Bickerdike, "5-HT2C Receptor Agonists as Potential Drugs for the Treatment of Obesity," Current Topics in Medicinal Chemistry, 3:885-897 (2003).

(56) References Cited

OTHER PUBLICATIONS

Biel, "Bronchodilators, N-substituted Derivatives of 1-(3',4'-Dihydroxyphenyl)-2-aminoethanol (Arterenol)," J. Am. Chem. Soc. 76:3149-3153 (1954).
Binetti et al. "Behavior Disorders in Alzheimer Disease: A Transcultural Perspective.," Arch Neurol., 55:539-544 (1998).
Bosch et al., "Studies on the Synthesis of Pentacyclic Strychnos Indole Alkaloids. Photocyclization of N-Chloroacetyl-l,2,3,4,5,6-hexahydro-1,5-methanoazocino [4,3-b] Indole Derivatives," Tetrahedron, 41(12):2557-66 (1985).
Bos et al., "Novel Agonists of 5HT2C receptors. Synthesis & biological evaluation of Substituted 2- {Indol-1-yl)-1-methylethylamines and 2-(Indeno[1,2-b]pyrrol-1-yl)-1-methylethylamines," Improved Therapeutics for Obsessive Compulsive Disorder, J. Med. Chem. 40(17):2762-2769 (1997).
Bremner "Seven Membered Rings," Institute for Biomolecular Science, Dept. of Chemistry, University of Wollongong; "Progress in Heterocyclic Chemistry 13," Pergamon Press, Ch. 7:340-77 (2001).
Callahan et al., "Fluoxetine Increases the Anorectic and Long-Term Dopamine-Depleting Effects of Phentermine," Synapse, 38(4):471-6 (2000).
Carey, F and Sunderg, R., "Advanced Organic Chemistry, Part B: Reactions and Synthesis, second edition" 1983, Plenum Press, New York, pp. 96-98.
CAS Registry No. 006640-24-01 (2007), 1 page.
CAS Registry No. 27487-50-9 (1984), 1 page.
CAS Registry No. 27487-51-0 (1984), 1 page.
CAS Registry No. 46906-45-0 (1984), 1 page.
CAS Registry No. 149454-12-6 (1993), 1 page.
CAS Registry No. 400878-20-8 (2002), 1 page.
CAS Registry No. 620948-34-7 and 620948-93-8 (2007), 2 pages.
Casy, et al., "Some Arylalkylamino Analogs of Acyclic Analgetics," J. Med. Chem., 11(3):599-601 (1968).
Chahal et al., IDdb Meeting Report 2000, May 17-18, 1 page.
Chang et al., "Dopamine Receptor Binding Properties of Some 2,3,4,5-tetrahydro-1H-3-benzazepine-7-ols with Non-Aromatic Substituents in the 5-Position," Bioorganic & Medicinal Chemistry Letters, 2(5):399-402 (1992).
Chemical abstract (online) Accession No. 1980:407990, 1 page.
Cheng, "Fen/Phen and Valvular Heart Disease: The Final Link Has Now Been Established," Circulation 2000;102;e180.
Chumpradit et al., "(±)-7-Chloro-8-hydroxyl-1-(4'-[125I]iodophenyl)-3-methyl-2,3,4,5-tetrahydro-1H-3-benzazepine: A Potential CNS D-1 Dopamine Receptor Imaging Agent," J. Med. Chem., 32:1431-35 (1989).
Clark et al., "1,9-Alkano-bridged 2,3,4,5-tetrahydro-1H-3-benzazepines with Affinity for the α2-Adrenoceptor and the 5-HT1A Receptor," J. Med. Chem., 33:633-41 (1990).
Clinical Trial NCT00768612. "Study Evaluating Safety and Tolerability of Vabicaserin in Patients With Sudden Worsening of Schizophrenia Study," (2008), 1 page.
Connolly et al., "Selections from Current Literature: Pharmacological Treatment of Obesity," Family Practice, 15(1):88-93 (1998).
Deady et al., "Synthesis of Some Tetrahydro-2- and 3-benzazepines, and of Hexahydro-3-benzazocine," JCS Perkin I, 782-3 (1973).
Demarinis et al., "Development of an Affinity Ligand for Purification of α2-Adrenoceptors from Human Platelet Membranes," J. Med. Chem., 27:918-921 (1984).
Dhonnchadha et al., "Anxiolytic-Like Effects of 5-HT2 Ligands on Three Mouse Models of Anxiety," Behav. Brain Res. 140:203-214 (2003).
Diagnostic and Statistical Manual of Mental Disorders, 4th edition, Text Revision, Washington, DC, American Psychiatric Association, 2000*, 1 page.
Di Chiara et al., "Nucleus Accumbens Shell and Core Dopamine: Differential Role in Behavior and Addiction," Behavioural Brain Research, 137: 75-114 (2002).
Di Chiara et al., "Reward System and Addiction: What Dopamine Does and Doesn't Do," Current Opinion in Pharmacology 7:69-76 (2007).

Di Giovanni et al., "Serotonin/Dopamine Interaction—Focus on 5-HT2C Receptor, a New Target of Psychotropic Drugs," Indian Journal of Experimental Biology, 40:1344-1352 (2002).
Di Matteo et al., "Role of 5-HT2C Receptors in the Control of Central Dopamine Function," Trends in Pharmacological Sciences, 22(5):229-232 (2001).
Dixit et al. "Agents Acting on Central Nervous System: Part XXIII-2-Substituted 1, 2, 3, 4, 6, 7, 12, 12a-Octahydropyrazino[2,1-b][3] benzazepines & 3-Substituted 1, 2, 3, 4, 4a, 5, 6, 11-Octahydropyrazino[I,2-b][2] benzazepines," CDRI Communication No. 1969, 893-97 (1974).
Draper et al., "Novel Stereoselective Syntheses of the Fused Benzazepine Dopamine D1 Antagonist (6aS, 13bR)-11-chloro-6, 6a,7,8,9, 13b-hexahydro-7-methyl-5H-benzo[d]naphth[2, 1-b]azepin-12-ol (Sch 39166): 1. Aziridinium Salt Based Syntheses," Organic Process Research & Development, 2(3):175-85 (1998).
Flannery-Schroeder, "Reducing Anxiety to Prevent Depression," Am. J. Prev. Med. 31 (6S1):S136-S142 (2006).
Frankel et al., "Brain Serotonin Transporterdistribution in Subjects With Impulsive Aggressivity: A Positron Emission Study With [11C]McN 5652." Am. J. Psychiatry,162:915-923 (2005).
Fuchs et al., "Total Synthesis of (+/−)-Lennoxamine and (+/−)-Aphanorphine by Intramolecular Electrophilic Aromatic Substitution Reactions of 2-Amidoacroleins," Organic Letters, 3(24):3923-3925 (2001).
Gallant et al., "U-22,394A: A Controlled Evaluation in Chronic Schizophrenic Patients," Current Therapy Research, 9(11):579-81(1967).
Gardent et al., "Sur Quelques Proprietes De L'amino-2-Bromo-4 1H Benzazepine-3 Et De Ses Derives," Bulletin de la Societe Chimique de France, 2:600-5 (1968).
Garrido., Form and Structure of Crystals, Chapter V, p. 204, 2000.
Garrison, "Defining Obesity: An Adventure in Cardiovascular Disease Epidemiology," J. Nutritional Biochem. 9(9):493-500 (1998).
Gerace et al., "Predictors of Weight Increases over 7 Years in Fire Fighters and Paramedics," Preventive Medicine 25:593-600 (1996).
Gerritz et al., "Two General Routes to 1,4-Disubstituted-2,3,4,5-tetrahydro-1H-3-benzazepines," Organic Letters, 2(25):4099-102 (2000).
Gobert et al., "Serotonin$_{2C}$ Receptors Tonically Suppress the Activity of Mesocortical Dopaminergic and Adrenergic, But Not Serotonergic, Pathways: A Combined Dialysis and Electrophysiological Analysis in the Rat," Synapse 36: 205-221 (2000).
Gombar et al., "Pharmacokinetics of a Series of 6-Chloro-2, 3, 4, 5-Tetrahydro-3-Substituted-1H-3-Benzazepines in Rats," Drug Metab. Disposition ,16:367-372 (1988).
Greene, "Protective Groups in Organic Synthesis," 3rd Ed., Wiley and Sons (1999)* ref excessively voluminous; provided upon request, 300 pages.
Greene et al., Protective Groups in Organic Syntheses, 2nd Ed., Wiley and Sons, NY (1991)* *ref excessively voluminous; provided upon request, 300 pages.
Griesser "Polymorphism in the Pharmaceutical Industry," ed. Rolf Hilfier, Wiley-VCH Verlag GmbH & Co.: pp. 211-233 (2006).
Guillory, "Polymorphism in Pharmaceutical Solids," ed. Harry G. Brittain, Marcel Dekker, Inc., vol. 95: pp. 202-209 (1999).
Halford et al., "Serotonergic Drugs: Effects on Appetite Expression and Use for the Treatment of Obesity," Drugs 67(1):27-55 (2007).
Halford et al., "o-Phenylenediacetimide and Other Compounds Related to 3,1H-benzazepine," J. Org. Chem., 17:1646-52 (1952).
Halford, "Obesity Drugs in Clinical Development," Current Opinion in Investigational Drugs 7(4):312-318 (2006).
Hasan et al., "Syntheses of N-Chloroacyl-β-phenylethylamine Derivatives," Indian J. Chem., 9:1022-4 (1971).
Hashima et al., "Syntheses and Biological Activities of the Marine Bryozoan Alkaloids Convolutamines A, C and F and Lutamides A and C," Bioorg & Med. Chem., 8:1757 (2000).
Hassine-Coniac, et al., "Preparation Et Propriétés D'aldéhydes Dans La Série De La Benzazépine-3," Bulletin de La Société Chimique de France, 11:3985-92 (1971) French Lang Only.
Haynes et al., "Occurrence of Pharmaceutically Acceptable Anions and Cations in the Cambridge Structural Database," J. Pharm. Sci. 94(10):2111-2120 (2005).

(56) References Cited

OTHER PUBLICATIONS

Hazebroucq, "Accès A Des I-H, Tètrahydro-2, 3, 4,5 Benzazèpines-3 One-I, et a Des Hexahydro Imidazo Isoquinoléines," Ann. Chim., t.I:221-54 (1966) French Lang Only.
Heisler et al., "Activation of Central Melanocortin Pathways by Fenfluramine," Science, 297:609-611 (2002).
Helferich et al., "Uber Derivate Einger Chinolincarbonsauren," J. Fur Praktische Chemie, 33:39-48 (1966).
Hester et al., "Azepinoindoles. I. Hexahydroazepino[4,5-b]indoles," J. Med. Chem., 11(1): 101-106 (1968).
Heys et al., "A New Entry into C7-Oxygenated Tetrahydro-1H-3-benzazepines: Efficient Labeling with Carbon-14 in the Benzo Ring," J. Org. Chem., 54(19):4702-6 (1989).
Higgins et al. "Serotonin and Drug Reward: Focus on 5-HT2C Receptors," European Journal of Pharmacology, 480: 151-162 (2003).
Hitzig, "Combined Serotonin and Dopamine Indirect Agonists Correct Alcohol Craving and Alcohol-Associated Neuroses," Journal of Substance Abuse Treatment, 11(5):489-90 (1994).
Ichii, "Friedel-Crafts Aralkylation. II. The AICI3 CH2NO2-Catalyzed Phenethylation of Benzene and Toluene With 2-Arylethyl Chlorides in a Nitromethane Solution," Bulletin of the Chemical Society of Japan, 45(9):2810-2813 (1972).
Im et al., "Positive Allosteric Modulator of the Human 5-HT2C Receptor," Molecular Pharmacology, 64: 78-84 (2003).
Isaac, "The 5-HT2C Receptor as a Potential Therapeutic Target for the Design of Antiobesity and Antiepileptic Drugs," Drugs of the Future 26(4), 383-393 (2001).
Jandacek, "APD-356 (Arena)," Current Opinion in Investigational Drugs 6(10):1051-1056 (2005).
Jenck, et al., "Antiaversive Effects of 5HT2C Receptor Agonists and Fluoxetine in a Model of Panic-Like Anxiety in Rats," European Neuropsychopharmacology 8: 161 (1998).
Jensen et al., "Potential Role of New Therapies in Modifying Cardiovascular Risk in Overweight Patients with Metabolic Risk Facts," Obesity 14 (Suppl. 3):143S-149S (2006).
Kaiser et al., "6-(Phenylthio)-substituted 2,3,4,5-tetrahydro-1H-3-benzazepines, a Novel Class of Dopamine Receptor Antagonists and Neuroleptics," J. Med. Chem., 23(9):975-6 (1980).
Karasu et al., Practice Guideline for the Treatment of Patients with Major Depressive Disorder (2000), 1 page.
Klein, "Outcome Success in Obesity," Obesity Res., 9(suppl. 4):354S-358S (2001).
Klohr et al., "An Intramolecular Photocyclization to Form the Azepino[3,4,5-cd]Indole System," Synthetic Communications 18(7):671-4 (1988).
Koplan et al., "Preventing Childhood Obesity: Health in the Balance, Executive Summary," The National Academies Press, Washington, D.C., 436 pages (excerpt includes pp. 1-19, v-xix) (2005).
Krull et al., "Synthesis and Structure/NMDA Receptor Affinity Relationships of 1-Substituted Tetrahydro-3-Benzazepines," Bioorganic & Medicinal Chem. 12(6):1439-1451 (2004).
Kuenburg et al., "Development of a Pilot Scale Process for the Anti-Alzheimer Drug (--)-Galanthamine Using Large-Scale Phenolic Oxidative Coupling and Crystallisation-Induced Chiral Conversion," Organic Process Research & Development, 3(6):425-31 (1999).
Lacivita et al., "Selective Agents for Serotonin2C (5-HTC2C) Receptor," Current Topics in Medicinal Chemistry, 6: 1927-1970 (2006).
Ladd et al., "Synthesis of a Dopaminergic Binding of 2-Aryldopamine Analogues: Phenethylamines, 3-Benzazepines, and 9-(Aminomethyl) Fluorenes," J. Med. Chem., 29(10):1904-12 (1986).
Lam et al., Canadian Consensus Guidelines for the Treatment of Seasonal Affective Disorder, Clinical & Academic Publishing, Vancouver, BC, Canada (1999), 1 page.
Lennon et al., "Azabenzocycloheptenones. Part XVIII. Amines and Amino-ketones of the Tetrahydro-3-benzazepin-1-one Series," J.C. S. Perkin I, 7:622-6 (1975).
Lin et al, "Benzindene Prostaglandins. Synthesis of Optically Pure 15-Deoxy-U-68,215 and its Enantiomer via a Modified Intramolecular Wadsworth-Emmons-Wittig Reaction," J. Org. Chem., 52(25):5594-601 (1987).
Loke et al., "Appetite Suppressants and Valvular Heart Disease—A Systematic Review," BMC Clinical Pharmacology, 2(6):1-10 (2002).
MacDonald et al., "Design and Synthesis of trans-3-(2-(4-((3-(3-(5-methyl-1,2,4-oxadiazolyl))-phenyl)carboxamido)cyclohexyl)pethyl)-7-methylsulfonyl-2,3,4,5-tetrahydro-1H-3-benzazepine (SB-414796): A Potent and Selective Dopamine D3 Receptor Antagonist," J. Med. Chem., 46(23):4952-64 (2003).
March, "Advanced Organic Chemistry, Reactions, Mechanisms and Structure; Third edition," 1985, John Wiley &Sons (Wiley-Interscience Publication), New-York, pp. 382-384.
Martin et al.,"5HT2C Receptor Agonists Pharmacological Characteristics and Therapeutic Potential," J. Pharmacol. Exp. Therap., 286(2):913-924 (1998).
Millan et al., "5HT2C Receptors Mediate Penile Erections in Rats: Actions of Novel and Selective Agonists and Antagonists." Eur. J. Pharmacol., 325:9-12 (1997).
Moline et al., "Postpartum Depression: A Guide for Patients and Families," Expert Consensus Guidelines Series—Treatment of Depression in Woman,112-113 (2001).
Mondeshka et al., "Racemische und optisch active 2-Chlorethylcarbamoyl-Derivate des 7,8-Dimethoxy-1-phenyl-1$H$-3-benzazepins: Neue Strukturtypen von DA, NE und 5-HT Uptake Inhibitoren," Arch. Pharm., 323:829-832 (1990).
Muller et al., "Intracellular 5-HT2C-Receptor Dephosphorylation: A New Target for Treating Drug Addiction," Trends in Pharmacological Sciences, 27(9):455-58 (2006).
Nagase et al., "An Anhydrous Polymorphic Form of Trehalose," Carbohydrate Research 337(2):167-173 (2002).
Nagle et al., "Efficient Synthesis of β-amino Bromides," Tetrahedron Letters, 41:3011-4 (2000).
Nair et al., "Preparation of 2,3,4,5-Tetrahydro-3,1H-benzazepine-2-one," Indian J. Chem., 5:169-70 (1967).
National Institute on Drug Abuse, Proc. 41st Ann. Scientific Mtg. 356-401 (1979).
Navarro-Vazquez et al., "A Study of Aryl Radical Cyclization in Enaminone Esters," J. Org. Chem., 67:3213-20 (2002).
Neumeyer et al., "Development of a High Affinity and Stereoselective Photoaffinity Label for the D-1 Dopamine Receptor: Synthesis and Resolution of 7-[125I]Iodo-8-hydroxy-3-methyl-1-(4'-azidophenyl)-2,3,4,5-tetrahydro-1H-3-benzazepine," J. Med. Chem., 33(2):521-6 (1990).
Niendam et al., "Neurocognitive Performance and Functional Disability in the Psychosis Prodrome," Schizophrenia Research, 84:100-111 (2006).
Ohnmacht et al., "Naphtho[2,1-b][1,5]-and [1,2-f][1,4]oxazocines as Selective NK1 Antagonists," Biorganic & Medicinal Chem. 12(10):2653-2666 (2004).
Okuno et al., "Photocyclization of N-chloroacetyl-2,5-dimethoxyphenethylamine. Synthesis of Pyrroloindoles," Chem. Pharm. Bull., 23(11):2584-90 (1975).
Orito et al., "Benzolactams-1: Alkylation of 1,2,4,5-Tetrahydro-3-Methyl-3H-3-Benzazepine-2-One With Sodium Hydride and Alkyl Halide," Tetrahedron 36:1017-1021 (1980).
Orito et al., "Total Synthesis of Pseudo Type of Protopine Alkaloids," Heterocycles, 14(1):11-14 (1980).
Orito, et al., "Synthetic Studies of Heterocyclic Compounds I. Alkylation and Acylation of 1,2,4,5- Tetrahydro-3-Methyl-3H-3-Benzazepin-2-one," CASREACT, 93:7990 (1979).
Paulekuhn et al., "Trends in Active Pharmaceutical Ingredient Salt Selection Based on Analysis of the Orange Book Database." J. Med. Chem., 50(26):6665-6672 (2007).
Pauvert et al., "Silver Nitrate-Promoted Ring Enlargement of 1-tribromomethyl-1,2-dihydro- and 1- tribromethyl-1,2, 3,4-tetrahydro-isoquinoline Derivatives: Application to the Synthesis of the Anti-anginal Zatebradine," Tetrahedron Letters, 44:4203-6 (2003).

(56) References Cited

OTHER PUBLICATIONS

Pawan et al., "Preliminary Study on the Effects of Fenfluramine Derivative, 'S992' in Man," British Journal of Pharmacology, 41(2): 416P-417P (1971).
Pecherer et al., "The Synthesis of Some 7- and 7,8-Substituted 2,3,4,5-tetrahydro-1H-3-benzazepines," J. Het. Chem., 8(5):779-783 (1971).
Pecherer et al., "A Novel Synthesis of Aromatic Methoxy and Methylenedioxy Substituted 2,3,4,5-tetrahydro-1H-3-benzazepines," J. Het. Chem., 9:609-16 (1972).
Perry et al., "Prospective Study of Risk Factors for Development on Non-Insulin Dependent Diabetes in Middle Aged British Men," BMJ, 310:560-564 (1995).
Pfeiffer et al., "Dopaminergic Activity of Substituted 6-Chloro-1-phenyl-2,3,4,5-tetrahydro-1H-3-benzazepines," J. Med. Chem., 25(4):352-8 (1982).
Piesla et al., "Atypical Antipsychotic-Like Effects of 5-HT2C Agonists," Schizophrenia Research 49:95 (2001).
Porras, et al., "5-HT2A and 5-HT2C/2B Receptor Subtypes Modulate Dopamine Release Induced in Vivo by Amphetamine and Morphine in Both the Rat Nucleus Accumbens and Striatum," Neuropsychopharmacology 26: 311-324 (2002).
Remington's Pharmaceutical Sciences 17th ed., Mack Publishing Company, Easton Pa.: xv-xvi, 1409-1423 (1985).
Rosenzweig-Lipson et al., "Vabicaserin: Effects of a Novel 5HT2C Agaonist on Medial Prefrontal Cortex Neurotransmission, Cognition and Sensorimotor Gating," 29th ECNP Congress, Vienna, Austria (2007).
Roth et al., "Anorectic Efficacy of the Fenfluramine/Phentermine Combination in Rats: Additivity or Synergy?" Eur. J. Pharmacol., 373(2-3):127-34 (1999).
Rothman, "Treatment of Alcohol and Cocaine Addiction by the Combination of Pemoline and Fenfluramine: A Preliminary Case Series," Journal of Substance Abuse Treatment, 12(6):449-53 (1995).
Rothman et al., "Evidence of Possible Involvement of 5-HT2B Receptors in the Cardiac Valvulopathy Associated with Fenfluramine and Other Serotonergic Medications," Circulation, 2836-41 (2000).
Rowland et al., "Acute Anorectic Effect of Single and Combined Drugs in Mice Using a Non-deprivation Protocol," Psychopharmacology (Berl), 157(2):193-6 (2001).
Rowland et al., "Anorectic Effect of Dehydroepiandrosterone Combined with Dexfenfluramine or Thionisoxetine," Eur. J. Pharmacol., 419(1):61-4 (2001).
Rowland et al., "Effects of the Cannabinoid Receptor Antagonist SR 141716, Alone and in Combination with Dexfenfluramine or Naloxone, on Food Intake in Rats," Psychopharmacology (Berl), 159(1):111-6 (2001).
Rowland et al., "Comparison of Either Norepinephrine-uptake Inhibitors or Phentermine Combined with Serotonergic Agents on Food Intake in Rats," Psychopharmacology (Berl), 149(1):77-83 (2000).
Schaffner et al., "Preventing Severe Mental Illnesses—New Prospects and Ethical Challenges," Schizophrenia Research, 51:3-15 (2001).
Schlademan et al., "Synthesis of Oxo- and 1-Hydroxy-azobenzocycloalkanes," J. Chem. Soc. Perkin Trans., 2:213-215 (1972).
Silverstone, "Appetite Suppressants: a Review." Drugs. 43:6, (1992). Abstract, 1 page.
Smith et al., "Discovery and SAR of New Benzazepines as Potent and Selective 5HT2c Receptor Agonists for the Treatment of Obesity," Bioorganic & Medicinal Chemistry Letters, 15(5):1467-1470 (2005).
Smith, "5-HT2C Receptor Agonists for the Treatment of Obesity," Presentation, Arena Pharmaceuticals, Inc., Jul. 28, 2010, 30 pages.
Smith, "Discovery of Lorcaserin (APD356): A Selective 5HT2C Agonist for the Treatment of Obesity," Presentation, Arena Pharmaceuticals, Inc., (2006).
Smith, et al., "Discovery and Structure—Activity Relationship of (1R)-8-Chloro-2,3,4,5-tetrahydro-1-methyl-1H-3-benzazepine (Lorcaserin), a Selective Serotonin 5-HT2c Receptor Agonist for the Treatment of Obesity," J. Med. Chem. 51:305-313 (2008).
Sussman et al., "Effects of Nefazodone on Body Weight: A Pooled Analysis of Selective Serotonin Reuptake Inhibitor- and Imipramine-Controlled Trails," J. Clin. Psychiatry, 62:4:256-60 (2001).
Tecott et al., "Eating Disorder and Epilepsy in Mice Lacking 5-HT2C Serotonin Receptors." Nature, 374:542-546 (1996).
Tietze et al., "Efficient Synthesis of 2, 3, 4, 5-Tetrahydro-1H-3-Benzazepines by Intramolecular Heck Reaction," Synthesis, 876-880 (1993).
Tohda et al., "Molecular Pathopharmacology of 5-HT2C Receptors and the RNA Editing in the Brain." J. Pharma. Science, 100: 427-432 (2006).
Tsuang et al., "Towards the Prevention of Schizophrenia," Biol. Psychiatry, 48:349-356 (2000).
Van Oekelen et al., "5-HT2A and 5-HT2C Receptors and Their Atypical Regulation Properties," Life Sciences, 72:2429-2449 (2003).
Vanderlaan et al., "Synthesis and Oxidative Coupling of (±)-3-Sxoreticuline," J. Org. Chem., 50(6):743-7 (1985).
Vink et al., "Risk Factors for Anxiety and Depression in the Elderly: A Review," J. Affect. Disord., 106:29-44 (2008).
Webb, "APD356, a Potential New Treatment for Obesity," Presentation, Arena Pharmaceuticals, Inc., Aug. 11, 2005, 43 pages.
Weinstock et al., "Separation of Potent Central and Renal Dopamine Agonist Activity in Substituted 6-Chloro-2,3,4,5-tetrahydro-7,8-dihydroxy-1-phenyl-1H-3-benzazepines," J. Med. Chem., 23(9):973-5 (1980).
Wellman et al., "Synergistic Interactions Between Fenfluramine and Phentermine," Int. J. Obes., 23(7):723-32 (1999).
Wilk, "Exchange Type Reactions Between Oxiranes or Thiiranes and 2-Hydroxyalkyl or 2-Thioalkyl Amines and Sulfides," Pol. J. Chem. 62:895 (1988).
Williams, Chemistry Demystified, pp. 123, 126 (2003).
Winkler, "Obesity and Hemostasis<" Archives of Gynecology & Obst. 261(1):25-29 (1997).
Wise, "Addiction Becomes a Brain Disease," Neuron, 26: 27-33 (2000).
Wisner et al., "Postpartum Depression," N. Engl. J. Med., 347(3):194-199 (2002).
Woods et al., "Annual Report: Evaluation of New Compounds for Opoid Activity," National Institute on Drug Abuse, Proceedings of the 41st Annual Scientific Meeting pp. 356-401 (1979).
Wu et al., "Amino Diol Based Asymmetric Syntheses of a Fused Benzazepine as a Selective D1 Dopamine Receptor," Organic Process Research & Development, 1(5):359-64 (1997).
Yasuda et al., "A Novel and Stereoselective Synthesis of (±)-Cephalotaxine and its Analogue," Tetrahedron Letters, 27(18):2023-6 (1986).
Yonemitsu et al., "Photolysis of N-Chloracetyl-O-methyl-L-tyrosine to an Azaazulene," J. Am. Chem. Soc.,, 89(4): 1039-40 (1967).
Yonemitsu et al., "Photocyclization of Pharmacodynamic Amines. IV. Novel Heterocycles from N-chloroacetyl-3,4-dimethoxyphenethylamine," J. Am. Chem. Soc., 92(19):5686-90 (1970).
Yonemitsu et al., "Photocyclization of Pharmacodynamic Amines. II. X-Ray Analysis of a Noncentrosymmetric Tetracyclic Indole," J. Am. Chem. Soc., 90(23):6522-3 (1968).
Yonemitsu et al., "Photocyclizations of Tyrosines, Tyramines, Catecholamines, and Normescaline," J. Am. Chem. Soc., 90(3):776-84 (1968).
Yoshinaga et al., "Prevention of Mildly Overweight Children from Development of More Overweight Condition," Prevention Medicine, 38:172-174 (2004).
Zhang et al., "Convolutamines A-E, Novel β-Phenylethylamine Alkaloids from Marine Bryozoan Amathia convolute," Chem. Lett., 12:2271-2274 (1994).

* cited by examiner

PROCESSES FOR THE PREPARATION OF INTERMEDIATES RELATED TO THE 5-HT$_{2C}$ AGONIST (R)-8-CHLORO-1-METHYL-2,3,4,5-TETRAHYDRO-1H-3-BENZAZEPINE

This is a 371 filing of PCT Application No. PCT/US09/001,340, filed Mar. 3, 2009, which claims benefit of U.S. Provisional Application No. 61/068,102, filed Mar. 4, 2008. Each of those applications is incorporated herein by reference in their entirety.

FIELD OF THE INVENTION

The present invention provides processes and intermediates useful in the preparation of (R)-8-chloro-1-methyl-2,3,4,5-tetrahydro-1H-3-benzazepine, a serotonin (5-HT) receptor agonist that is useful in the treatment or prophylaxis of, for example, central nervous system disorders, such as obesity.

BACKGROUND OF THE INVENTION

Serotonin (5-HT) neurotransmission plays an important role in numerous physiological processes both in neurological and in psychiatric disorders. For example, 5-HT has been implicated in the regulation of feeding behavior. 5-HT is believed to work by inducing a feeling of fullness or satiety so eating stops earlier and fewer calories are consumed. It has been shown that a stimulatory action of 5-HT on the 5HT$_{2C}$ receptor plays an important role in the control of eating. Furthermore, stimulation of the 5HT$_{2C}$ receptor has also been shown to play an important role in the anti-obesity effect of d-fenfluramine. As the 5-HT$_{2C}$ receptor is expressed in high density in the brain (notably in the limbic structures, extrapyramidal pathways, thalamus and hypothalamus specifically in the PVN and DMH, and predominantly in the choroid plexus) and is expressed in low density or is absent in peripheral tissues, a selective 5-HT$_{2C}$ receptor agonist can be a more effective and safe anti-obesity agent. Also, 5-HT$_{2C}$ knockout mice are overweight with cognitive impairment and susceptibility to seizure. Thus, the 5HT$_{2C}$ receptor is recognized as a well-accepted receptor target for the treatment of obesity, psychiatric disorders, and other disorders.

In view of the growing demand for compounds useful in the treatment of disorders related to the 5-HT$_{2C}$ receptor, (R)-8-chloro-1-methyl-2,3,4,5-tetrahydro-1H-3-benzazepine has emerged has an important new compound. Accordingly, new and more efficient routes leading to (R)-8-chloro-1-methyl-2,3,4,5-tetrahydro-1H-3-benzazepine and intermediates related thereto are needed. The processes and compounds described herein help meet these and other needs.

SUMMARY OF THE INVENTION

The processes and intermediates of the present invention are useful in preparing (R)-8-chloro-1-methyl-2,3,4,5-tetrahydro-1H-3-benzazepine having Formula (I):

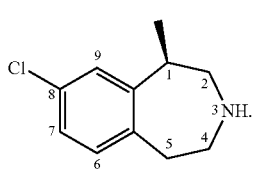

(I)

This compound is useful in the treatment of 5-HT$_{2C}$ receptor associated disorders, such as, obesity, and is disclosed in PCT patent publication, WO2003/086303.

Some embodiments of the present invention disclose processes for preparing 2-(4-chlorophenyl)ethyl bromide comprising the steps:

reacting hydrogen bromide with 2-(4-chlorophenyl)ethanol to form a reaction mixture comprising the 2-(4-chlorophenyl)ethyl bromide;

and isolating the 2-(4-chlorophenyl)ethyl bromide from the reaction mixture.

Some embodiments of the present invention disclose processes for preparing 2-chloro-N-(4-chlorophenethyl)propan-1-amine hydrochloride comprising the steps:

a) reacting hydrogen bromide with 2-(4-chlorophenyl)ethanol to form 2-(4-chlorophenyl)ethyl bromide;

b) reacting said 2-(4-chlorophenyl)ethyl bromide with 1-aminopropan-2-ol to form 1-(4-chlorophenethylamino)propan-2-ol; and c) reacting said 1-(4-chlorophenethylamino)propan-2-ol with thionyl chloride to form 2-chloro-N-(4-chlorophenethyl)propan-1-amine hydrochloride.

DETAILED DESCRIPTION OF EMBODIMENTS OF THE INVENTION

The processes and intermediates of the present invention are useful in the preparation of the therapeutic agent (R)-8-chloro-1-methyl-2,3,4,5-tetrahydro-1H-3-benzazepine, including, salts and crystal forms thereof. The compound (R)-8-chloro-1-methyl-2,3,4,5-tetrahydro-1H-3-benzazepine, including, salts and crystal forms are disclosed in PCT patent publications, WO2003/086306 and WO2006/069363.

Certain processes for the preparation of compounds of Formula (I) and salts thereof are disclosed in PCT patent publications, WO2005/019179 and WO2007/120517.

Intermediates useful in the preparation of (R)-8-chloro-1-methyl-2,3,4,5-tetrahydro-1H-3-benzazepine, HCl salts and crystal forms thereof, include 2-(4-chlorophenyl)ethyl bromide and 2-chloro-N-(4-chlorophenethyl)propan-1-amine hydrochloride.

Several improvements and advantages have now been discovered for the preparation of each and are described herein. Conversion of the Commercially Available Compound 2-(4-chlorophenyl)ethanol to 2-(4-chlorophenyl)ethyl bromide with the use of HBr.

In some embodiments, 2-(4-chlorophenyl)-ethyl bromide can be prepared from the commercially available compound, 2-(4-chlorophenyl)ethanol, according to the process depicted in Synthetic Scheme 1.

Synthetic Scheme 1

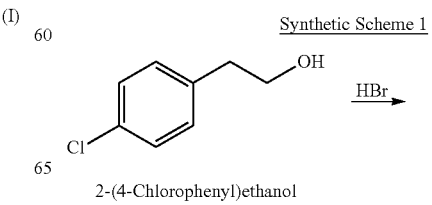

2-(4-Chlorophenyl)ethanol

-continued

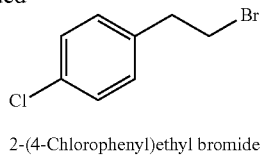

2-(4-Chlorophenyl)ethyl bromide

Accordingly, in some embodiments, the invention discloses processes for preparing 2-(4-chlorophenyl)ethyl bromide comprising reacting hydrogen bromide with 2-(4-chlorophenyl)ethanol to form 2-(4-chlorophenyl)ethyl bromide.

In some embodiments, the present invention discloses processes for preparing 2-(4-chlorophenyl)ethyl bromide comprising the steps:

reacting hydrogen bromide with 2-(4-chlorophenyl)ethanol to form a reaction mixture comprising the 2-(4-chlorophenyl)ethyl bromide; and isolating the 2-(4-chlorophenyl)ethyl bromide from the reaction mixture.

In some embodiments, the reacting of hydrogen bromide with 2-(4-chlorophenyl)ethanol is conducted in the absence of an added solvent. The phrase "absence of an added solvent" is intended to mean that none or no substantial amount of solvent is added to the reaction (e.g. the reaction can be conducted "neat" in the absence of solvent). It is understood that during the reaction an equivalent amount of water is formed together with 2-(4-chlorophenyl)ethyl bromide and that this water so formed is not considered as a solvent but merely as a co-product for purposes of this definition. It is further understood that any impurity present in 2-(4-chlorophenyl)ethanol in an amount of about 5% or less as determined by HPLC does not constitute "an added solvent" for the purposes of this definition.

In some embodiments, the reacting of hydrogen bromide with 2-(4-chlorophenyl)ethanol is conducted by adding the hydrogen bromide to the 2-(4-chlorophenyl)ethanol.

In some embodiments, the reacting of hydrogen bromide with 2-(4-chlorophenyl)ethanol is conducted by adding the hydrogen bromide as a gas to the 2-(4-chlorophenyl)ethanol.

In some embodiments, the reacting of hydrogen bromide with 2-(4-chlorophenyl)ethanol is conducted by adding the hydrogen bromide as a gas above the surface of the 2-(4-chlorophenyl)ethanol. In some embodiments, the pressure above the surface of the 2-(4-chlorophenyl)ethanol is about +2 bar to about ambient pressure. In some embodiments, the pressure above the surface of the 2-(4-chlorophenyl)ethanol is about +1.65 bar to about +0.5 bar.

In some embodiments, the reacting of hydrogen bromide with 2-(4-chlorophenyl)ethanol is conducted by adding the hydrogen bromide as a gas below the surface of the 2-(4-chlorophenyl)ethanol.

In some embodiments, the reacting of hydrogen bromide with 2-(4-chlorophenyl)ethanol is conducted at a temperature from about 25° C. to about 110° C.

In some embodiments, the reacting of hydrogen bromide with 2-(4-chlorophenyl)ethanol is conducted at a temperature from about 60° C. to about 100° C.

In some embodiments, the reacting of hydrogen bromide with 2-(4-chlorophenyl)ethanol is conducted at a temperature from about 70° C. to about 90° C.

In some embodiments, the reacting of hydrogen bromide with 2-(4-chlorophenyl)ethanol is conducted at a pressure from about −1.00 bar to about +2.00 bar.

In some embodiments, the reacting of hydrogen bromide with 2-(4-chlorophenyl)ethanol is conducted at a pressure from about −1.00 bar to about +0.50 bar.

In some embodiments, the reacting of hydrogen bromide with 2-(4-chlorophenyl)ethanol is conducted at a pressure from about −0.85 bar to about +0.37 bar.

In some embodiments, isolating comprises separating the water co-product from the 2-(4-chlorophenyl)ethyl bromide.

In some embodiments, after the isolating step, 2-(4-chlorophenyl)ethyl bromide has a purity of about 95% or greater as determined by HPLC. In some embodiments, after the isolating step, 2-(4-chlorophenyl)ethyl bromide has a purity of about 97% or greater as determined by HPLC. The term "HPLC" refers to High Performance Liquid Chromatography. In some embodiments, "HPLC" refers to Reversed-Phase High Performance Liquid Chromatography. In some embodiments, "HPLC" refers to Normal-Phase High Performance Liquid Chromatography.

Conversion of the Commercially Available Compound 2-(4-chlorophenyl)ethanol to 2-chloro-N-(4-chlorophenethyl)propan-1-amine.

In some embodiments, 2-chloro-N-(4-chlorophenethyl)propan-1-amine hydrochloride can be prepared from 2-(4-chlorophenyl)ethanol according to the process depicted in Synthetic Scheme 2.

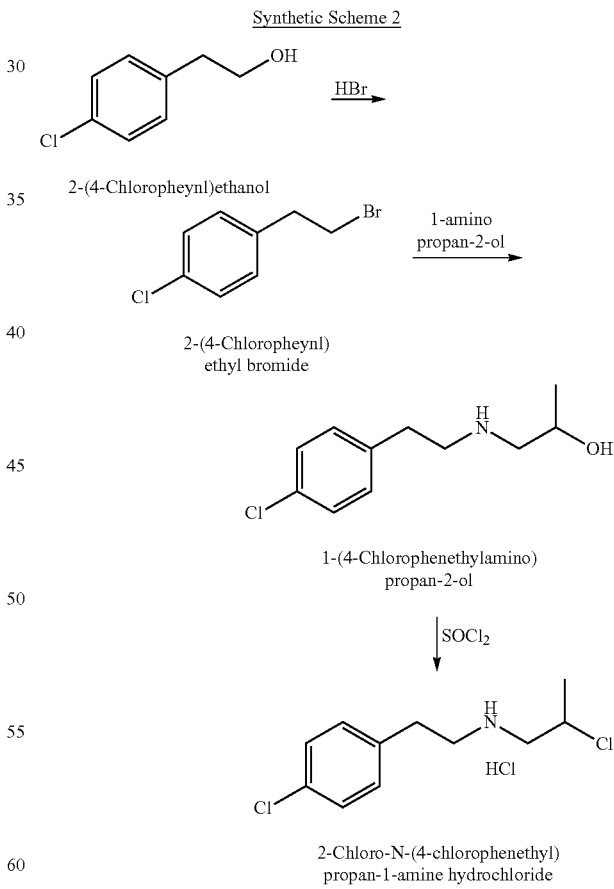

Synthetic Scheme 2

2-(4-Chloropheynl)ethanol 2-(4-Chloropheynl) ethyl bromide 1-(4-Chlorophenethylamino) propan-2-ol 2-Chloro-N-(4-chlorophenethyl) propan-1-amine hydrochloride In some embodiments, the present invention discloses processes for preparing 2-chloro-N-(4-chlorophenethyl)propan-1-amine hydrochloride comprising the steps:

a) reacting hydrogen bromide with 2-(4-chlorophenyl)ethanol to form 2-(4-chlorophenyl)ethyl bromide;

b) reacting the 2-(4-chlorophenyl)ethyl bromide with 1-aminopropan-2-ol to form 1-(4-chlorophenethylamino)propan-2-ol; and c) reacting the 1-(4-chlorophenethylamino)propan-2-ol with thionyl chloride to form 2-chloro-N-(4-chlorophenethyl)propan-1-amine hydrochloride.

In some embodiments, reacting hydrogen bromide with 2-(4-chlorophenyl)ethanol is conducted in the absence of an added solvent.

In some embodiments, reacting hydrogen bromide with 2-(4-chlorophenyl)ethanol is conducted by adding the hydrogen bromide to the 2-(4-chlorophenyl)ethanol.

In some embodiments, reacting hydrogen bromide with said 2-(4-chlorophenyl)ethanol is conducted by adding said hydrogen bromide as a gas to said 2-(4-chlorophenyl)ethanol.

In some embodiments, reacting hydrogen bromide with 2-(4-chlorophenyl)ethanol is conducted at a temperature from about 25° C. to about 110° C.

In some embodiments, reacting hydrogen bromide with 2-(4-chlorophenyl)ethanol is conducted at a temperature from about 60° C. to about 100° C.

In some embodiments, reacting hydrogen bromide with 2-(4-chlorophenyl)ethanol is conducted at a temperature from about 70° C. to about 90° C.

In some embodiments, reacting hydrogen bromide with 2-(4-chlorophenyl)ethanol is conducted at a pressure from about −1.00 bar to about +2.00 bar.

In some embodiments, reacting hydrogen bromide with 2-(4-chlorophenyl)ethanol is conducted at a pressure from about −1.00 bar to about +0.50 bar.

In some embodiments, reacting hydrogen bromide with 2-(4-chlorophenyl)ethanol is conducted at a pressure from about −0.85 bar to about +0.37 bar.

In some embodiments, reacting hydrogen bromide with 2-(4-chlorophenyl)ethanol, produces 2-(4-chlorophenyl)ethyl bromide with a purity of about 95% or greater as determined by HPLC. In some embodiments, reacting hydrogen bromide with 2-(4-chlorophenyl)ethanol, produces 2-(4-chlorophenyl)ethyl bromide with a purity of about 97% or greater as determined by HPLC. In some embodiments, "HPLC" refers to Reversed-Phase High Performance Liquid Chromatography. In some embodiments, "HPLC" refers to Normal-Phase High Performance Liquid Chromatography.

In some embodiments, reacting 2-(4-chlorophenyl)ethyl bromide with 1-aminopropan-2-ol is conducted by the addition of 2-(4-chlorophenyl)ethyl bromide to 1-aminopropan-2-ol.

In some embodiments, reacting 2-(4-chlorophenyl)ethyl bromide with 1-aminopropan-2-ol is conducted by the addition of 2-(4-chlorophenyl)ethyl bromide to 1-aminopropan-2-ol at a rate such that 1-(bis(4-chlorophenethyl)amino)propan-2-ol is formed in an amount less than about 10% compared to 1-(4-chlorophenethylamino)propan-2-ol as determined by HPLC.

In some embodiments, reacting 2-(4-chlorophenyl)ethyl bromide with 1-aminopropan-2-ol is conducted by the addition of 2-(4-chlorophenyl)ethyl bromide to 1-aminopropan-2-ol at a rate such that 1-(bis(4-chlorophenethyl)amino)propan-2-ol is formed in an amount less than about 5% compared to 1-(4-chlorophenethylamino)propan-2-ol as determined by HPLC. The chemical structure for 1-(bis(4-chlorophenethyl)amino)propan-2-ol is shown below:

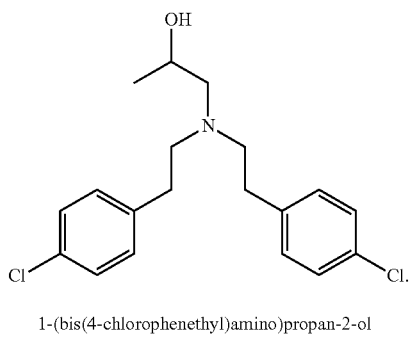 [SMILES: CC(O)CN(CCc1ccc(Cl)cc1)CCc1ccc(Cl)cc1]

1-(bis(4-chlorophenethyl)amino)propan-2-ol

In some embodiments, reacting 2-(4-chlorophenyl)ethyl bromide with 1-aminopropan-2-ol is conducted in the presence of a molar excess of 1-aminopropan-2-ol compared to 2-(4-chlorophenyl)ethyl bromide.

In some embodiments, reacting 2-(4-chlorophenyl)ethyl bromide with 1-aminopropan-2-ol is conducted in the presence of about 5 molar excess of 1-aminopropan-2-ol compared to 2-(4-chlorophenyl)ethyl bromide.

In some embodiments, reacting 2-(4-chlorophenyl)ethyl bromide with 1-aminopropan-2-ol is conducted at a temperature from about 60° C. to about 95° C.

In some embodiments, reacting 2-(4-chlorophenyl)ethyl bromide with 1-aminopropan-2-ol is conducted at a temperature from about 75° C. to about 90° C.

In some embodiments, reacting 1-(4-chlorophenethylamino)propan-2-ol with thionyl chloride is conducted in the presence of a solvent. In some embodiments, the solvent is an aromatic hydrocarbon. In some embodiments, the solvent comprises toluene. In some embodiments, the solvent is toluene.

In some embodiments, reacting 1-(4-chlorophenethylamino)propan-2-ol with thionyl chloride is conducted in the presence of dimethylacetamide (also referred to as DMA).

In some embodiments, reacting 1-(4-chlorophenethylamino)propan-2-ol with thionyl chloride is conducted in the presence of dimethylformamide (also referred to as DMF).

In some embodiments, reacting 1-(4-chlorophenethylamino)propan-2-ol with thionyl chloride is conducted at a temperature from about 55° C. to about 70° C.

In some embodiments, reacting 1-(4-chlorophenethylamino)propan-2-ol with thionyl chloride is conducted at a temperature from about 60° C. to about 65° C.

In some embodiments, the process further comprises a step of separating a water co-product from the 2-(4-chlorophenyl)ethyl bromide after step a) and prior to step b).

In some embodiments, wherein after step a) the resulting mixture is used in step b) without substantial purification.

In some embodiments, the process further comprises a step of removing 1-aminopropan-2-ol from the mixture after step b) and prior to step c). In some embodiments, the removing of 1-aminopropan-2-ol from the mixture after step b) is conducted by the steps comprising:

adding water and an immiscible organic solvent to the mixture after step b) to form a biphasic mixture comprising an aqueous phase and an organic phase;

mixing the biphasic mixture and subsequently allowing to separate into the aqueous phase and the organic phase; and removing the aqueous phase from the organic phase.

In some embodiments, the immiscible organic solvent comprises toluene.

In some embodiments, the immiscible organic solvent is toluene.

In some embodiments, the process further comprises a step of crystallizing the 2-chloro-N-(4-chlorophenethyl)propan-1-amine hydrochloride after step c). In some embodiments, crystallizing the 2-chloro-N-(4-chlorophenethyl)propan-1-amine hydrochloride is conducted in the presence of a mixture comprising a $C_1$-$C_6$ alcohol. In some embodiments, crystallizing the 2-chloro-N-(4-chlorophenethyl)propan-1-amine hydrochloride is conducted in the presence of a mixture comprising isopropanol.

In some embodiments, steps a), b) and c) are conducted without substantial purification and in doing so steps a), b) and c) are considered to be "telescoped" steps. The phrase "without substantial purification" is intended to mean that little or no substantial purification is utilized, such as, chromatography (reverse-phase chromatography, normal-phase chromatography, flash, HPLC, MPLC, etc.), distillation (vacuum or atmospheric) of product, etc. It is understood that, 1) the mere removal of water by phase separation, where the water was either a co-product of the reaction or physically added; 2) the removal of a volatile solvent (i.e. a liquid with a boiling point of about 150° C. or less at atmospheric pressure); and 3) recrystallization and crystallization, are not considered substantial purification steps for purposes of this definition.

In some embodiments, after reacting 1-(4-chlorophenethylamino)propan-2-ol with thionyl chloride, produces 2-chloro-N-(4-chlorophenethyl)propan-1-amine hydrochloride with a purity of about 95% or greater as determined by HPLC. In some embodiments, after reacting 1-(4-chlorophenethylamino)propan-2-ol with thionyl chloride, the 2-chloro-N-(4-chlorophenethyl)propan-1-amine hydrochloride with a purity of about 98% or greater as determined by HPLC. In some embodiments, "HPLC" refers to Reversed-Phase High Performance Liquid Chromatography. In some embodiments, "HPLC" refers to Normal-Phase High Performance Liquid Chromatography.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

Preparation of 2-(4-chlorophenyl)ethyl bromide from 2-(4-chlorophenyl)ethanol

In a 1 L pressure vessel, 4-chlorophenylethanol (412.8 g, 2636 mmol) was stirred and heated to an internal temperature of ~91° C. The system was held under reduced pressure (~−0.98 bar) for ~2 min. Hydrogen bromide gas was gradually charged into the pressure vessel and the reaction was stirred at an internal pressure between +0.69 and +1.65 bar for 135 min. The vessel was allowed to slowly vent to a caustic scrubber and flushed with nitrogen gas for 5 min. Conversion to the bromide was found to be 4.27% by HPLC. The reaction mixture was allowed to cool to ambient temperature overnight under nitrogen. The mixture was then heated once more in an oil bath set at 96° C. and the vessel was evacuated. The vessel was gradually filled with hydrogen bromide gas and stirred at an internal pressure between +1.38 and +1.65 bar for 2 h. Conversion to the bromide was found to be 92.67% by HPLC. The reaction was held at a bath temperature of 96° C. at atmospheric pressure for 45 min. The vessel was then evacuated and slowly backfilled with hydrogen bromide gas over 15 min to +1.38 bar. After stirring for a further 2.5 h at +1.24 to +1.38 bar, the vessel was vented to the caustic scrubber and held at a bath temperature of 96° C. in closed system at atmospheric pressure. Conversion to the bromide was found to be 99.49% by HPLC with a peak area purity of 98.71%.

In order to test stability and impurity formation, the pressure vessel was then evacuated and gradually back filled with hydrogen bromide gas to an internal pressure of +1.03 bar. The dark brown suspension was allowed to stir at +1.03 bar at a bath temperature of 96° C. After 15 h the internal pressure had risen to +2.41 bar and the vessel was vented to the caustic scrubber, purged with nitrogen, and allowed to cool to ambient temperature. The peak area purity was found to be 96.06%. The reaction mixture was transferred to a separatory funnel and allowed to separate at room temp. The upper product phase was washed with water (412 mL) in 2 portions to leave a milky beige suspension (563.4 g) with an HPLC peak area purity of 99.29%.

Example 2

Preparation of 2-(4-chlorophenyl)ethyl bromide from 2-(4-chlorophenyl)ethanol 2-(4-Chlorophenyl)ethanol (1600 kg, 10.22 mol) was heated with stirring in a jacketed reaction to 70° C. After the reactor had been evacuated to −0.85 bar and sealed, hydrogen bromide gas was bubbled into the liquid 2-(4-chlorophenyl)ethanol while allowing the heat of reaction to warm the stirred reaction mixture to 90° C. The hydrogen bromide gas addition was continued sufficiently slowly to maintain the stirred reactor contents at 90° C. with reactor jacket cooling. When 1072 kg (13.25 mol) of hydrogen bromide gas had been added, the reactor pressure was +0.37 bar, and HPLC analysis of the reaction mixture's upper organic phase revealed percentage peak areas of 96.0 and 1.63 for 2-(4-chlorophenyl)ethyl bromide and 2-(4-chlorophenyl)ethanol respectively. The stirred reaction mixture was vented to a caustic scrubber and cooled to 30° C. The reaction mixture was then allowed to stand for 130 min to permit phase separation. The lower aqueous HBr phase (490 kg) was drained at 29° C. To remove as much residual hydrogen bromide as possible before the final water wash, the stirred upper product phase was sparged with nitrogen at atmospheric pressure for 77 minutes at 30° C., evacuated to −0.85 bar, sparged with nitrogen again and maintained under reduced pressure for one hour at 30° C. Water (445 kg) was then added, and the resulting stirred mixture was sparged with nitrogen at 30° C. for 2 h. The reactor contents were then allowed to stand for 3 h to permit phase separation. The milky lower product phase was drained from the clear upper aqueous phase. The upper aqueous phase weighed 465 kg. The lower product phase weighed 2190 kg (97.7% yield not corrected for assay) and was found to have an HPLC peak area purity of 98.0%.

Example 3

Preparation of 2-chloro-N-(4-chlorophenethyl)propan-1-amine Hydrochloride

In a 65 mL glass pressure vessel, 4-chlorophenylethanol (32.725 g, 209 mmol) was warmed to between 90 and 100° C. The vessel was charged with hydrogen bromide gas and the mixture was stirred at +1.38 to +1.93 bar for 4.5 h. The pressure was released and the reaction showed 99.18% conversion by HPLC. The mixture was allowed to cool to room temperature to leave 2-(4-chlorophenyl)ethyl bromide as a brown liquid (53.735 g).

Without purification, this was then added with stirring to a 100 mL round-bottom flask containing 1-aminopropan-2-ol (83 mL, 1046 mmol) at 85° C. The clear yellow mixture was stirred at 85 to 95° C. for 2 h, at which time LCMS indicated 100% conversion. The reaction was allowed to cool to room temperature overnight and then warmed to 75° C. to form a yellow oil. Water (23 mL) was added followed by toluene (96 mL) maintaining the temperature between 70 and 75° C. and the resulting mixture was stirred at this temperature for 15 min. The mixture was allowed to separate and the lower aqueous layer was extracted with toluene. The combined organic layers were concentrated to leave 1-(4-chlorophenethylamino)propan-2-ol as a yellow oil.

The oil was suspended in toluene (179 mL) and warmed to 50° C. to dissolve. N,N-Dimethylacetamide (5.88 mL, 62.7 mmol) was added followed by thionyl chloride (19.38 mL, 266 mmol) dropwise while maintaining the internal temperature at <60° C. On completion of the addition, the reaction was stirred at between 60 and 65° C. for 4 h. LCMS indicated 100% conversion to the chloride. The reaction was allowed to cool to room temperature and filtered. The cake was washed with toluene and dried on the filter overnight. The dried solids were suspended in isopropanol (85.8 mL) and water (7.2 mL) and the stirred mixture was heated to reflux for 1 h then cooled to between 12 and 15° C. over 1 h. The mixture was stirred at this temperature for 1 h, cooled further to 0 to 3° C. and stirred for an additional 1 h. The slurry was filtered and the cake was washed with isopropanol and dried under reduced pressure at 70° C. to leave the title compound as an off white solid (37.719 g, 67.2%; 100% peak area purity by HPLC).

Example 4

Representative HPLC Conditions

Representative HPLC Condition A.
Reagents: Water (Milli-Q or equivalent), Acetonitrile (supragradient HPLC grade from Scharlau, Art. No. Ac0331, or equivalent); o-Phosphoric acid, 84-85%, r.g. from Scharlau (Art. No. Ac1100) or equivalent.
Run Time: 60 minutes.
Equilibration time: 8 minutes
Solvents: Acetonitrile/Water/o-Phosphoric acid (50/50/1 v/v/w).
Sample Size: δ 4, Injection with needle-wash (solvent).
Column: MZ-Aqua Perfect C18, 3 pm, 250×4.0 mm (Supplier. EGT-Chemie AG, Art. No: 250.4, 0.0610.N).
Mobile Phase A: Water.
Mobile Phase B: Acetonitrile.
Mobile Phase C: Water/o-phosphoric acid (1 L/50 g).
Gradient:

| Time (min) | % of A | % of B | % of C |
|---|---|---|---|
| 0 | 76 | 14 | 10 |
| 5 | 76 | 14 | 10 |
| 35 | 74 | 16 | 10 |
| 60 | 0 | 90 | 10 |

Flow Rate: 1.0 mL/minute.
Temperature: 40° C.
Detection wavelength: UV, 195 nm.

Representative HPLC Condition B.
Reagents: Water (Milli-Q or equivalent), Acetonitrile (supragradient HPLC grade from Scharlau, Art. No. Ac0331, or equivalent); Trifluoroacetic acid (TFA), HPLC grade or equivalent.
Run Time: 23 minutes.
Equilibration time: 8 minutes
Sample Size: 5 µL, Injection with needle-wash (solvent).
Column: Luna C18 (2), 150×4.6 mm, 3 µm.
Mobile Phase A: Water (0.03% TFA).
Mobile Phase B: Acetonitrile (0.025% TFA).
Gradient:

| Time (min) | % of A | % of B |
|---|---|---|
| 0 | 82 | 18 |
| 10 | 70 | 30 |
| 23 | 20 | 80 |

Flow Rate: 1.5 mL/minute.
Temperature: 35° C.
Detection wavelength: UV, 220 nm.

Example 5

Preparation of 2-(4-chlorophenyl)ethyl bromide from 2-(4-chlorophenyl)ethanol

The quantities in the following procedure are normalized to 1.00 kg of the starting material 2-(4-chlorophenyl)ethanol. The yield shown below is the average from four separate production runs using 1600-2400 kg of the starting material 2-(4-chlorophenyl)ethanol, the following quantities and volume ratios.

| Starting Material and Product Quantities for 2-(4-chlorophenyl)ethyl bromide | | | | |
|---|---|---|---|---|
| Starting Material or Product | Mol. Wt. | Use | Kg | Mole Ratio |
| 2-(4-chlorophenyl)ethanol | 156.61 | Starting Material | 1.00 | 1.00 |
| Hydrogen Bromide | 80.91 | Reagent | 0.669 | 1.296 |
| Water | 18.02 | Product Wash | 0.278 | |
| 2-(4-chlorophenyl)ethyl bromide | 219.51 | Product | 1.375 | 0.981 |

| Volumes for Conversion of 2-(4-chlorophenyl)ethanol to 2-(4-chlorophenyl)ethyl bromide | | | |
|---|---|---|---|
| L/Kg, 2-(4-chlorophenyl)ethanol | | L/Kg, 2-(4-chlorophenyl)ethyl bromide | |
| Max. | Min. | Max. | Min. |
| 1.670 | 0.864 | 1.215 | 0.629 |

To a reactor was charged 2-(4-chlorophenyl)ethanol (1.00 kg, 1.00 mol equivalent). The reactor contents were stirred and heated to 70° C. and purged with several cycles of evacuation and refilling with nitrogen. After the final evacuation, HBr gas was sparged into the stirred reactor contents (subsurface) and the temperature of the reaction mixture was allowed to increase from about 70° C. to about 90° C. The HBr gas was continued into the stirred reaction mixture at a sufficient rate to maintain the reactor pressure at or below 20 psig and the temperature of the reactor contents at about 85-95° C. with reactor jacket cooling. After the HBr gas uptake slows, samples of the crude reaction mixture were obtained to determine conversion of 2-(4-chlorophenyl)ethanol to 2-(4-chlorophenyl)ethyl bromide. After the conversion was achieved [2-(4-chlorophenyl)ethanol <2% by HPLC peak area, typically one hour after addition of 0.669 kg (1.296 mol equiv.) of HBr gas] the reactor was vented to atmospheric pressure through a caustic scrubber and cooled to approximately 30° C. The reaction mixture was allowed to stand for about two hours to provide two phases. The lower aqueous HBr byproduct phase (0.281 kg) was drained to waste. The resulting crude product was sparged with nitrogen gas at 30° C. and atmospheric pressure for about 75 minutes to remove as much residual hydrogen bromide as possible before the final water wash. The reactor was evacuated and the nitrogen sparging of nitrogen was continued through the stirred crude product at 30° C. for about an hour while continuing to pull full vacuum. To the resulting crude product was charged with water (0.278 kg) the contents stirred at 30° C. for 15 minutes. The stirring was stopped and the phases were allowed to separate at 30° C. over 2 to 3 hours. The lower product phase, 2-(4-chlorophenyl)ethyl bromide, 1.375 kg, 98.1% yield not corrected for assay, 98.0 area % pure by HPLC, was separated from the upper aqueous phase (0.296 kg).

Observed times required to achieve ≥98.4% conversion of 2-(4-chlorophenyl)ethanol to 2-(4-chlorophenyl)ethyl bromide ranged from approximately 6 hours at 413 g laboratory scale to approximately 35 hours at 2400 kg scale. At 2400 kg scale, the rate-limiting factor was vaporization of HBr from the supply cylinders, not gas-liquid mass transfer in the reactor.

Various modifications of the invention, in addition to those described herein, will be apparent to those skilled in the art from the foregoing description. Such modifications are also intended to fall within the scope of the appended claims.

What is claimed is:

1. A process for preparing 2-chloro-N-(4-chlorophenethyl)propan-1-amine hydrochloride comprising the steps:
    a) reacting hydrogen bromide with 2-(4-chlorophenyl)ethanol to form 2-(4-chlorophenyl)ethyl bromide by adding said hydrogen bromide as a gas to said 2-(4-chlorophenyl)ethanol at a temperature from about 60° C. to about 100° C. and at a pressure from about −1.00 bar to about +2.00 bar in the absence of an added solvent;
    b) reacting said 2-(4-chlorophenyl)ethyl bromide with 1-aminopropan-2-ol to form 1-(4-chlorophenethylamino)propan-2-ol; and
    c) reacting said 1-(4-chlorophenethylamino)propan-2-ol with thionyl chloride to form 2-chloro-N-(4-chlorophenethyl)propan-1-amine hydrochloride.

2. The process according to claim 1, wherein said reacting hydrogen bromide with 2-(4-chlorophenyl)ethanol is conducted at a temperature from about 70° C. to about 90° C.

3. The process according to claim 1, wherein said reacting hydrogen bromide with 2-(4-chlorophenyl)ethanol is conducted at a pressure from about −1.00 bar to about +0.50 bar.

4. The process according to claim 1, wherein said reacting hydrogen bromide with 2-(4-chlorophenyl)ethanol is conducted at a pressure from about −0.85 bar to about +0.37 bar.

5. The process according to claim 1, wherein after said reacting hydrogen bromide with 2-(4-chlorophenyl)ethanol, produces said 2-(4-chlorophenyl)ethyl bromide with a purity of about 95% or greater as determined by HPLC.

6. The process according to claim 1, wherein after said reacting hydrogen bromide with 2-(4-chlorophenyl)ethanol, produces said 2-(4-chlorophenyl)ethyl bromide with a purity of about 97% or greater as determined by HPLC.

7. The process according to claim 1, wherein said reacting 2-(4-chlorophenyl)ethyl bromide with 1-aminopropan-2-ol is conducted by the addition of 2-(4-chlorophenyl)ethyl bromide to 1-aminopropan-2-ol.

8. The process according to claim 1, wherein said reacting 2-(4-chlorophenyl)ethyl bromide with 1-aminopropan-2-ol is conducted by the addition of 2-(4-chlorophenyl)ethyl bromide to 1-aminopropan-2-ol at a rate such that 1-(bis(4-chlorophenethyl)amino)propan-2-ol is formed in an amount less than about 10% compared to 1-(4-chlorophenethylamino)propan-2-ol as determined by HPLC.

9. The process according to claim 1, wherein said reacting 2-(4-chlorophenyl)ethyl bromide with 1-aminopropan-2-ol is conducted by the addition of 2-(4-chlorophenyl)ethyl bromide to 1-aminopropan-2-ol at a rate such that 1-(bis(4-chlorophenethyl)amino)propan-2-ol is formed in an amount less than about 5% compared to 1-(4-chlorophenethylamino)propan-2-ol as determined by HPLC.

10. The process according to claim 1, wherein said reacting 2-(4-chlorophenyl)ethyl bromide with 1-aminopropan-2-ol is conducted in the presence of a molar excess of 1-aminopropan-2-ol compared to 2-(4-chlorophenyl)ethyl bromide.

11. The process according to claim 1, wherein said reacting 2-(4-chlorophenyl)ethyl bromide with 1-aminopropan-2-ol is conducted at a temperature from about 60° C. to about 95° C.

12. The process according to claim 1, wherein said reacting 2-(4-chlorophenyl)ethyl bromide with 1-aminopropan-2-ol is conducted at a temperature from about 75° C. to about 90° C.

13. The process according to claim 1, wherein said reacting 1-(4-chlorophenethylamino)propan-2-ol with thionyl chloride is conducted in the presence of a solvent.

14. The process according to claim 13, wherein said solvent comprises toluene.

15. The process according to claim 1, wherein said reacting 1-(4-chlorophenethylamino)propan-2-ol with thionyl chloride is conducted in the presence of dimethylacetamide.

16. The process according to claim 1, wherein said reacting 1-(4-chlorophenethylamino)propan-2-ol with thionyl chloride is conducted at a temperature from about 55° C. to about 70° C.

17. The process according to any one of claims 1 to 15, wherein said reacting 1-(4-chlorophenethylamino)propan-2-ol with thionyl chloride is conducted at a temperature from about 60° C. to about 65° C.

18. The process according to claim 1, further comprising a step of separating a water co-product from said 2-(4-chlorophenyl)ethyl bromide after step a) and prior to step b).

19. The process according to claim 1, wherein after step a) the resulting mixture is used in step b) without substantial purification.

20. The process according to claim 1, further comprising a step of removing 1-aminopropan-2-ol from the mixture after step b) and prior to step c).

21. The process according to claim 20, wherein said removing 1-aminopropan-2-ol from the mixture after step b) is conducted by the steps comprising:
    adding water and an immiscible organic solvent to the mixture after step b) to form a biphasic mixture comprising an aqueous phase and an organic phase;
    mixing said biphasic mixture and subsequently allowing to separate into said aqueous phase and said organic phase; and
    removing said aqueous phase from said organic phase.

22. The process according to claim 21, wherein said immiscible organic solvent comprises toluene.

23. The process according to claim 21, wherein said immiscible organic solvent is toluene.

24. The process according to claim 1, further comprising a step of crystallizing said 2-chloro-N-(4-chlorophenethyl)propan-1-amine hydrochloride after step c).

25. The process according to claim 24, wherein said crystallizing said 2-chloro-N-(4-chlorophenethyl)propan-1-amine hydrochloride is conducted in the presence of a mixture comprising a $C_1$-$C_6$ alcohol.

26. The process according to claim 24, wherein said crystallizing said 2-chloro-N-(4-chlorophenethyl)propan-1-amine hydrochloride is conducted in the presence of a mixture comprising isopropanol.

27. The process according to claim 1, wherein steps a), b) and c) are conducted without substantial purification.

28. The process according to claim 1, wherein said reacting 1-(4-chlorophenethylamino)propan-2-ol with thionyl chloride, produces said 2-chloro-N-(4-chlorophenethyl)propan-1-amine hydrochloride with a purity of about 95% or greater as determined by HPLC.

29. The process according to claim 1, wherein said reacting 1-(4-chlorophenethylamino)propan-2-ol with thionyl chloride, produces said 2-chloro-N-(4-chlorophenethyl)propan-1-amine hydrochloride with a purity of about 98% or greater as determined by HPLC.

* * * * *